United States Patent
Sendai (10) Patent No.: US 7,477,393 B2
(45) Date of Patent: Jan. 13, 2009

(54) SPECIMEN ANALYSIS SYSTEM OBTAINING CHARACTERISTIC OF SPECIMEN BY DIFFUSION APPROXIMATION

(75) Inventor: Tomonari Sendai, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 293 days.

(21) Appl. No.: 11/523,501

(22) Filed: Sep. 20, 2006

(65) Prior Publication Data

US 2007/0073157 A1 Mar. 29, 2007

(30) Foreign Application Priority Data

Sep. 20, 2005 (JP) ............................. 2005-272169

(51) Int. Cl.
*G01N 21/00* (2006.01)
*A61B 5/00* (2006.01)
(52) U.S. Cl. ...................... 356/432; 600/310; 600/473
(58) Field of Classification Search ......... 356/432–440, 356/335–343; 600/310, 322, 323, 473, 476; 250/339.11, 341.8
See application file for complete search history.

(56) References Cited

U.S. PATENT DOCUMENTS

| | | | | | |
|---|---|---|---|---|---|
| 5,057,695 | A | * | 10/1991 | Hirao et al. ................. 250/575 |
| 5,277,181 | A | * | 1/1994 | Mendelson et al. ......... 600/322 |
| 5,372,135 | A | * | 12/1994 | Mendelson et al. ......... 600/322 |
| 5,517,987 | A | * | 5/1996 | Tsuchiya .................... 600/328 |
| 5,770,454 | A | * | 6/1998 | Essenpreis et al. .......... 436/164 |
| 5,825,488 | A | * | 10/1998 | Kohl et al. .................. 356/342 |
| 6,615,061 | B1 | * | 9/2003 | Khalil et al. ................ 600/310 |
| 2002/0084417 | A1 | * | 7/2002 | Khalil et al. ............. 250/341.8 |
| 2006/0015021 | A1 | * | 1/2006 | Cheng ........................ 600/310 |

OTHER PUBLICATIONS

M. Vauhkonen et al, "Utilizing the radiative transfer equation in optical tomography", OSA Biomedical Optics, pp. WF48-50, 2004.
L. Marti-Lopez et al., "Interpretation of the failure of the time-independent diffusion equation near a point source," Optics Communications, vol. 242, pp. 23-43, 2004.

* cited by examiner

*Primary Examiner*—Hoa Q Pham
(74) *Attorney, Agent, or Firm*—Sughrue Mion, PLLC

(57) ABSTRACT

In a specimen analysis system: a light injection unit selectively injects unscattered light and scattered light into a specimen at an incident position on the specimen, and an information processing unit performs calculation of a characteristic of the specimen by diffusion approximation, where the calculation of the characteristic in a near-incident-point region located within a predetermined distance from the incident position is based on information carried by light which exits from the near-incident-point region of the specimen in response to injection of the scattered light into the specimen, and the calculation of the characteristic in a remote region located farther from the incident position than the near-incident-point region is based on information carried by light which exits from the remote region in response to injection of the unscattered light into the specimen.

12 Claims, 5 Drawing Sheets

SPECIMEN ANALYSIS SYSTEM OBTAINING CHARACTERISTIC OF SPECIMEN BY DIFFUSION APPROXIMATION

BACKGROUND OF THE INVENTION

1. Field of the Invention

The present invention relates to a specimen analysis system which analyzes a characteristic of a specimen by injecting light into the specimen and acquiring information carried by light which propagates in and exits from the specimen.

2. Description of the Related Art

In recent years, the development of light absorption analysis (spectrometry) of a light-scattering substance such as a biological substance has been proceeding. The light applied to a light-scattering substance such as a biological substance undergoes multiple scattering and absorption in the light-scattering substance, and exits from the light-scattering substance. The behavior of light in a light-scattering substance can be expressed by an optical diffusion equation based on the optical diffusion theory, and the optical diffusion equation can be expressed as a differential equation. Therefore, it is possible to obtain a distribution of values of an optical characteristic such as an absorption coefficient, a scattering coefficient, or the like of a biological substance by measuring light which exits from the biological substance, and substituting the measured values in the optical diffusion equation.

For example, systems using the time-resolved spectroscopy or systems using the frequency-domain spectroscopy have been proposed as systems in which a distribution of optical characteristic values is obtained as above. The time-resolved spectroscopy uses ultra-short pulsed light having a width of approximately a picosecond, and the frequency-domain spectroscopy uses high-frequency modulated light.

According to the time-resolved spectroscopy, it is possible to obtain a distribution of optical characteristic values in a specimen of a light-scattering substance on the basis of the optical diffusion equation by injecting pulsed light into the specimen, and measuring the time spread (time profile) of the pulsed light which exits from the specimen after propagation through the specimen, where the time spread is caused by scattering of the pulsed light in the specimen.

According to the frequency-domain spectroscopy, it is possible to obtain a distribution of optical characteristic values in a specimen of a light-scattering substance on the basis of the optical diffusion equation by injecting high-frequency modulated light into the specimen, and measuring the intensity variation and phase delay at the modulation frequency in the light which exits from the specimen after propagation through the specimen, as disclosed by M. Vauhkonen et al., in "Utilizing the radiative transfer equation in optical tomography," OSA Biomedical Optics, pp. WF48-50, 2004.

However, when light is injected into a specimen as a biological substance or the like, and a distribution of optical characteristic values in the specimen is calculated by using the optical diffusion equation, the accuracy of the calculation deteriorates since the light is forward scattered in the vicinity of the incident point of the light. As disclosed by L. Marti-Lopez et al., "Interpretation of the failure of the time-independent diffusion equation near a point source," Optics Communications, vol. 242, pp. 23-43, 2004 a technique for solving the above problem has been proposed. According to this technique, a radiative transfer equation, instead of the optical diffusion equation, is used for calculating a distribution of optical characteristic values or the like in a vicinity of the incident point of the light in a specimen. For example, when the radiative transfer equation is used in calculation based on measurement results obtained from a near-incident-point region at distances less than 5 mm from the incident point of the light, and the optical diffusion equation is used in calculation based on measurement results obtained from farther regions at distances equal to or greater than 5 mm from the incident point of the light, it is possible to increase the accuracy in calculation of the distribution of the optical characteristic values or the like in the entire volume of the specimen including the vicinity of the incident point of the light (i.e., the near-incident-point region) and the other regions far from the incident point.

Nevertheless, the radiative transfer equation is much more complex than the optical diffusion equation. Therefore, when the radiative transfer equation is used in calculation of a distribution of optical characteristic values or the like in a specimen, the calculation time increases.

SUMMARY OF THE INVENTION

The present invention has been developed in view of the above circumstances.

The object of the present invention is to provide a specimen analysis system which can achieve high accuracy in calculation of a distribution of optical characteristic values in the entire volume of a specimen including the vicinity of the incident point of light and other regions far from the incident point without increase in the time necessary for the calculation, and enables reliable analysis of the specimen.

In order to accomplish the above object, a specimen analysis system according to the first aspect of the present invention is provided. The specimen analysis system according to the first aspect of the present invention comprises: a light injection unit which selectively injects unscattered light and scattered light into a specimen at an incident position on the specimen, where the scattered light is generated by scattering by a scattering medium; an information acquisition unit which acquires first information carried by first light exiting from a plurality of positions in a first region of the specimen in response to injection of the scattered light into the specimen, and second information carried by second light exiting from a plurality of positions in a second region of the specimen in response to injection of the unscattered light into the specimen, where the first region is located within a predetermined distance from the incident position, and the second region is located farther from the incident position than the first region; and an information processing unit which performs calculation of a characteristic of the specimen by diffusion approximation, where the calculation of the characteristic in the first region is based on the first information, and the calculation of the characteristic in the second region is based on the second information.

Preferably, the above specimen analysis system according to the first aspect of the present invention may further have the following additional features (i) and (ii).

(i) The light injection unit may alternately apply the unscattered light and the scattered light to the specimen.

(ii) The information acquisition unit may further acquire third information carried by third light exiting from a plurality of positions in a third region of the specimen in response to injection of the unscattered light into the specimen, and fourth information carried by fourth light exiting from a plurality of positions in the third region of the specimen in response to injection of the scattered light into the specimen, where the third region is located farther from the incident position than the first region and nearer to the incident position than the second region, and the information processing unit may compare the third information and the fourth information, and calculate the characteristic in the third region on the basis of the third information when the difference between the third information and the fourth information is equal to or smaller than a predetermined amount, and on the basis of the fourth information when the difference between the third information and the fourth information is greater than the predetermined amount.

In addition, in order to accomplish the aforementioned object, a specimen analysis system according to the second aspect of the present invention is also provided. The specimen analysis system according to the second aspect of the present invention comprises: a light injection unit which contains a scattering medium scattering unscattered light to a degree of scattering which can be controlled stepwise or continuously, produces first light and second light by scattering the unscattered light with the scattering medium to first and second degrees of scattering, respectively, and selectively injects the first light and the second light into a specimen at an incident position on the specimen, where the first degree of scattering is higher than the second degree of scattering; a scattering control unit which controls the degree of scattering in the scattering medium; an information acquisition unit which acquires first information carried by third light exiting from a plurality of positions in a first region of the specimen in response to injection of the first light into the specimen, and second information carried by fourth light exiting from a plurality of positions in a second region of the specimen in response to injection of the second light into the specimen, where the first region is located within a predetermined distance from the incident position, and the second region is located farther from the incident position than the first region; and an information processing unit which performs calculation of a characteristic of the specimen by diffusion approximation, where the calculation of the characteristic in the first region is based on the first information, and the calculation of the characteristic in the second region is based on the second information.

In the specimen analysis system according to the second aspect of the present invention, the second degree of scattering may be no scattering. That is, the second light according to the second aspect of the present invention may be unscattered light.

Preferably, in the above specimen analysis system according to the second aspect of the present invention, the information processing unit may compare the first information and the second information, and control the degree of scattering in the scattering medium according to the result of the comparison.

Further, the aforementioned first, second, third, and fourth light which exit from the specimen in the specimen analysis system according to the first aspect of the present invention and the aforementioned third and fourth light which exit from the specimen in the specimen analysis system according to the second aspect of the present invention are light which propagates in and exits from the specimen in response to the injection of the unscattered light or the scattered light in the specimen analysis system according to the first aspect of the present invention or in response to the injection of the first or second light in the specimen analysis system according to the second aspect of the present invention, and may be, for example, the light which is injected into the specimen and then propagates and diffuses through the specimen, or fluorescence emitted from the specimen, or autofluorescence which is spontaneously emitted from the specimen, or fluorescence emitted from a fluorescent agent which is added to the specimen in advance.

The advantages of the present invention are as follows.

(a) In the specimen analysis system according to the first aspect of the present invention, the light injection unit selectively injects unscattered light and scattered light into the specimen at an incident position on the specimen, and the characteristic in the first region (within a predetermined distance from the incident position) is calculated based on the first information (carried by first light exiting from a plurality of positions in a first region of the specimen in response to injection of the scattered light into the specimen), and the characteristic in the second region (located farther from the incident position than the first region) is calculated based on the second information (carried by second light exiting from a plurality of positions in a second region of the specimen in response to injection of the unscattered light into the specimen). Therefore, the diffusion approximation can be used even in the first region (near-incident-point region), so that it is possible to improve the accuracy in calculation of the characteristic (such as the optical scattering coefficient and the optical absorption coefficient) in the entire volume of the examined portion 9 including the first region (near-incident-point region) and the second region (remote region) without increasing the calculation time, and perform highly reliable analysis.

In addition, in the region where the diffusion approximation can be used with injection of the unscattered light, information carried by light exiting from the region of a specimen in response to injection of unscattered light into the specimen is approximately equal to information carried by light exiting from the region of the specimen in response to injection of scattered light into the specimen. On the other hand, in the region located so near to the incident position that the diffusion approximation cannot be used with unscattered light, information carried by light exiting from the region of the specimen in response to injection of the unscattered light into the specimen does not represent the actual state of the region in the specimen, although information carried by light exiting from the region of the specimen in response to injection of scattered light into the specimen approximately represents the actual state of the region in the specimen. Therefore, a substantial difference occurs between the information obtained by injection of the unscattered light and the information obtained by injection of the scattered light.

In consideration of the above situation, in the specimen analysis system according to the first aspect of the present invention having the aforementioned additional feature (ii), the information acquisition unit acquires the third information (carried by the third light exiting from the plurality of positions in the third region of the specimen in response to injection of the unscattered light into the specimen) and the fourth information (carried by the fourth light exiting from the plurality of positions in the third region of the specimen in response to injection of the scattered light into the specimen), where the third region (intermediate region) is located between the aforementioned first region (near-incident-point region) and the aforementioned second region (remote region). Then, the information processing unit compares the third information and the fourth information, and calculates the characteristic in the third region on the basis of the third information (obtained in response to injection of the unscattered light) when the difference between the third and fourth information is equal to or smaller than the predetermined amount (i.e., when the diffusion approximation can be used with injection of the unscattered light), and on the basis of the fourth information (obtained in response to injection of the scattered light) when the difference between the third and fourth information is greater than the predetermined amount (i.e., when the diffusion approximation cannot be used with the unscattered light). Therefore, it is possible to perform measurement by using unscattered light (which enables securement of high intensity of detected light) in the region to which the diffusion approximation can be used with injection of the unscattered light, and by using scattered light in the regions to which the diffusion approximation cannot be used with the unscattered light, so that it is possible to suppress increase in the time necessary for calculation of the characteristic of the specimen, and secure accuracy in the calculation.

(b) In the specimen analysis system according to the second aspect of the present invention, the characteristic of the specimen is measured by using the aforementioned first light (produced by scattering the scattered light with the scattering medium to the first (high) degree of scattering) for the aforementioned first region (near-incident-point region) located within the predetermined distance from the incident position, and by using the aforementioned second light (produced by scattering the unscattered light with the scattering medium to the second (low) degree of scattering) for the aforementioned second region (remote region) located farther from the incident position than the first region. That is, the diffusion approximation can be used even in the near-incident-point region. Therefore, it is possible to improve the accuracy in calculation of the characteristic in the entire volume of the specimen including the near-incident-point region and the remote region without increasing the calculation time, and perform highly reliable analysis.

Further, in the case where the information processing unit performs a comparison between the first information and the second information and controls the degree of scattering in the scattering medium according to the result of the comparison in the above specimen analysis system according to the second aspect of the present invention, it is possible to perform measurement by using, as the injected light, light which is scattered to such a degree as to enable use of the diffusion approximation. Therefore, it is possible to increase the accuracy in calculation of the characteristic in the entire volume of the specimen including the near-incident-point region and the remote region without increasing the calculation time while securing high intensity of detected light.

DESCRIPTION OF PREFERRED EMBODIMENTS

Preferred embodiments of the present invention are explained in detail below with reference to drawings. In the drawings, equivalent elements and constituents are indicated by the same reference numbers even in drawings for different embodiments, and descriptions of the equivalent elements or constituents are not repeated in the following explanations unless necessary.

First Embodiment

A specimen analysis system according to the first embodiment of the present invention is explained below with reference to FIGS. 1A and 1B, which schematically show the construction of the specimen analysis system according to the first embodiment.

The specimen analysis system 1 according to the first embodiment applies unscattered incident light L1 and scattered incident light L2 to an examined portion 9 of a subject dosed in advance with a fluorescent agent having an affinity for a tumor, and measures the distribution of the fluorescent agent in the examined portion 9, where the unscattered incident light L1 and scattered incident light L2 have wavelengths in the range which enables excitation of the fluorescent agent. In this example, the fluorescent agent emits fluorescence having a wavelength of 770 to 790 nm when the fluorescent agent is excited with light having the wavelength of 750 nm.

Figure 1A:
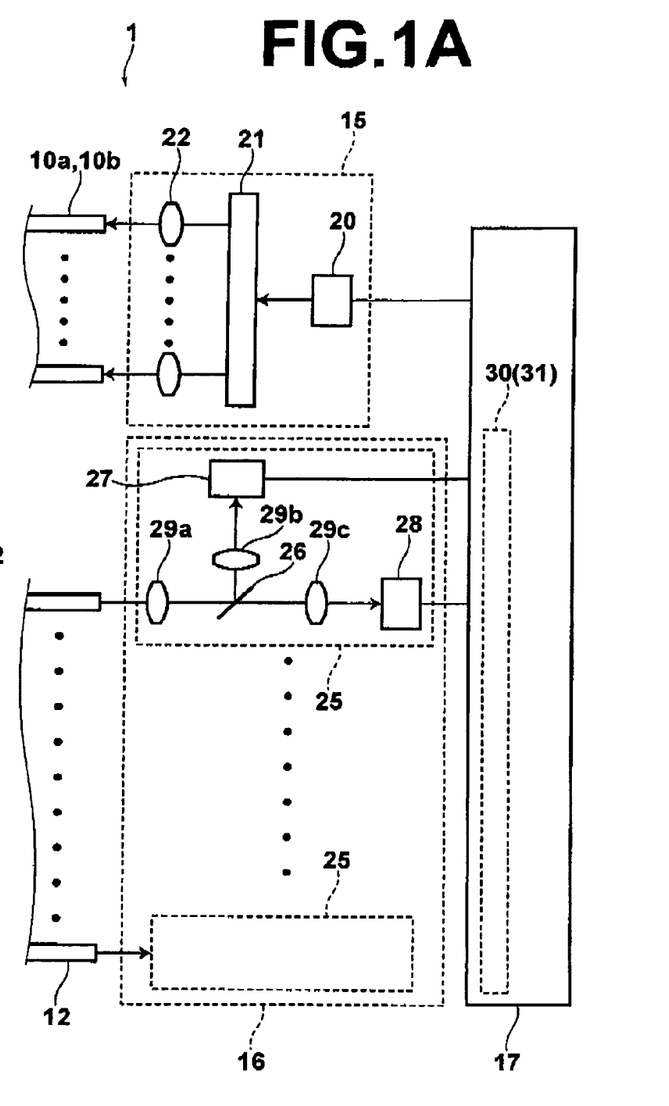
FIGS. 1A and 1B are diagrams schematically illustrating a specimen analysis system according to a first embodiment of the present invention.
Figure 1B:
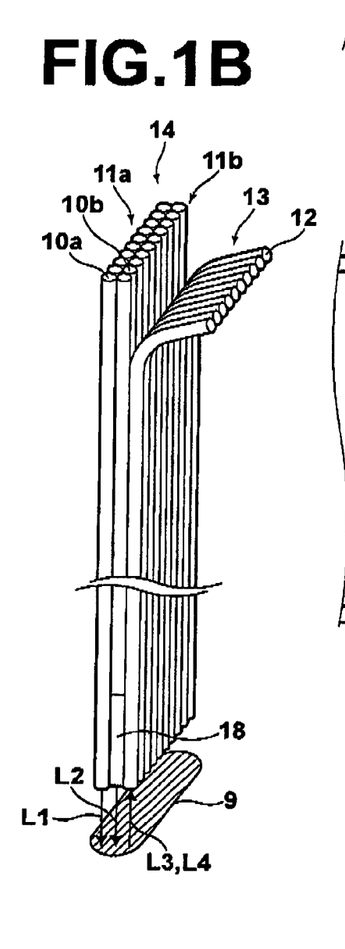

As illustrated in FIGS. 1A and 1B, the specimen analysis system 1 according to the first embodiment comprises an optical probe unit 14, a light-source unit 15, a measurement unit 16, and a signal-processing-and-control unit 17. The optical probe unit 14 is constituted by an unscattered-incident-light injector 11a, a scattered-incident-light injector 11b, and a detected-light guiding unit 13, which are arranged parallel to each other. The unscattered-incident-light injector 11a is constituted by a (one-dimensional) array of a hundred light-injection optical fibers 10a, and the scattered-incident-light injector 11b is constituted by a scatterer 18 and a (one-dimensional) array of a hundred light-injection optical fibers 10b, where the scatterer 18 is arranged at the ends of the light-injection optical fibers 10b on one side. The detected-light guiding unit 13 is constituted by an array of a hundred detection optical fibers 12. The unscattered-incident-light injector 11a and the scattered-incident-light injector 11b are connected to the light-source unit 15, and the detected-light guiding unit 13 is connected to the measurement unit 16. The light-source unit 15 and the measurement unit 16 are connected to the signal-processing-and-control unit 17.

Figure 2:
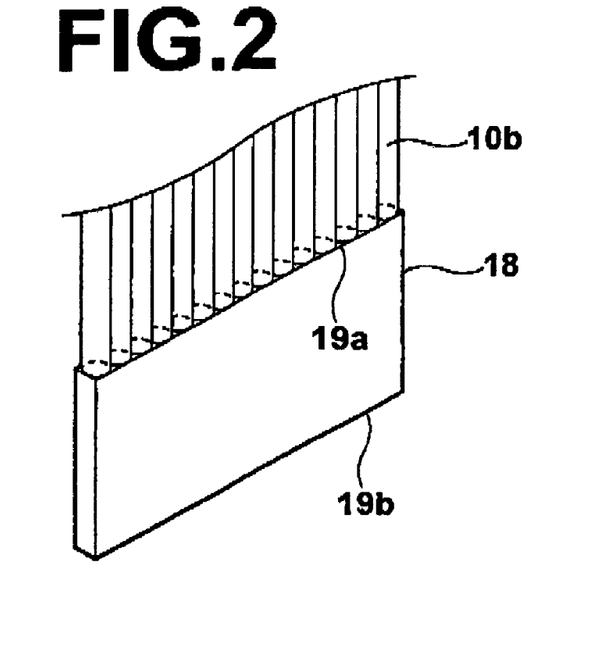
FIG. 2 is a diagram schematically illustrating an arrangement of a scatterer.

Each of the light-injection optical fibers 10a, the light-injection optical fibers 10b, and the detection optical fibers 12 has a total diameter of 100 micrometers, a core diameter of 80 micrometers, and a cladding thickness of 10 micrometers. The scatterer 18 is constituted by particles of solidified polyethylene latex, and formed into a plate having a lateral length of 1 centimeter, a height of 5 millimeters, and a thickness of 100 micrometers. FIG. 2 is a diagram schematically illustrating the arrangement of the scatterer 18 and the ends of the light-injection optical fibers 10b. As illustrated in FIG. 2, the ends of the light-injection optical fibers 10b abut an end face 19a of the scatterer 18, and the opposite end face 19b of the scatterer 18 faces the examined portion 9.

The light-source unit 15 is constituted by a light source 20, an optical switch 21, and two hundred lenses 22. The light source 20 emits as the unscattered incident light L1 pulsed light having the wavelength of 750 nm, the pulse width of 100 picoseconds (ps), and the average power of 3 mW at the repetition rate of 100 MHz. The light-injection optical fibers 10a and 10b are alternately arranged on the output side of the optical switch 21, and the lenses 22 are arranged between the output ends of the optical switch 21 and alternately arranged ones of the light-injection optical fibers 10a and 10b. The optical switch 21 injects the unscattered incident light L1 into the alternately arranged ones of the light-injection optical fibers 10a and 10b in succession through the lenses 22.

The measurement unit 16 is constituted by a hundred optical measurement units 25, to which the detection optical fibers 12 are respectively connected. Each of the optical measurement units 25 comprises a dichroic mirror 26, photon-counting circuits 27 and 28, and lenses 29a, 29b, and 29c. The light which exits from each of the detection optical fibers 12 is incident on the dichroic mirror 26 through the lens 29a in the corresponding one of the optical measurement units 25. When the wavelength of the light incident on the dichroic mirror 26 is equal to or longer than 760 nm, the light incident on the dichroic mirror 26 passes through the dichroic mirror 26. When the wavelength of the light incident on the dichroic mirror 26 is shorter than 760 nm, the dichroic mirror 26 reflects the light incident on the dichroic mirror 26 toward the direction perpendicular to the incident direction. The photon-counting circuit 27 counts the number of photons having a wavelength shorter than 760 nm and being detected during each measurement period, and the photon-counting circuit 28 counts the number of photons having a wavelength equal to or longer than 760 nm and being detected during each measurement period. Each of the photon-counting circuits 27 and 28 is constituted by a high-speed photodetector and a time-amplitude detector (TAC) (which are not shown), and measures the time difference between the timings of the injection of each light pulse and detection of a photon. The outputs of the photon-counting circuits 27 and 28 are supplied to the signal-processing-and-control unit 17.

The signal-processing-and-control unit 17 controls the overall operations of the specimen analysis system 1, and comprises a signal-processing unit 30, which calculates the distribution of the fluorescent agent in the examined portion 9. In addition, the signal-processing-and-control unit 17 produces a tine profile on the basis of the output of each of the photon-counting circuits 27 and 28 as illustrated in FIG. 2. Details of the operations of the signal-processing-and-control unit 17 are explained later.

The operations of the specimen analysis system 1 according to the first embodiment are explained below.

First, the optical probe unit 14 is brought into contact with the examined portion 9 of the subject, who may have a tumor. Since the optical probe unit 14 is held in contact with the examined portion 9 during measurement, the end of the optical probe unit 14 on the examined-portion side is protected by a transparent protective member (not shown).

Next, the operations for measurement are started under control of the signal-processing-and-control unit 17. The light source 20 in the light-source unit 15 emits the pulsed, unscattered incident light L1 having the wavelength of 750 nm, the pulse width of 100 ps, and the average power of 3 mW at the repetition rate of 100 MHz. The optical switch 21 injects the unscattered incident light L1 into the alternately arranged ones of the light-injection optical fibers 10a and 10b in succession. At this time, the optical switch 21 injects a million successive light pulses into each of the light-injection optical fibers 10a and 10b before injection into the next one of the light-injection optical fibers 10a and 10b.

The unscattered incident light L1 which is injected into the light-injection optical fibers 10a propagates through the light-injection optical fibers 10a, and is then incident on the examined portion 9. On the other hand, the unscattered incident light L1 which is injected into the light-injection optical fibers 10b propagates through the light-injection optical fibers 10b, and then enters the scatterer 18, in which the unscattered incident light L1 is scattered. A portion of the light L1 scattered in the scatterer 18 exits from the end face 19b as the scattered incident light L2, and is then incident on the examined portion 9.

While the unscattered incident light L1 is injected into the light-injection optical fibers 10a and 10b, the optical measurement units 25 (to which the detection optical fibers 12 are respectively connected) perform operations for measurement. When the unscattered incident light L1 is injected into the examined portion 9, scattered light L3 generated by scattering of the unscattered incident light L1 in the examined portion 9 and fluorescence L4 emitted from the fluorescent agent in the examined portion 9 propagate in and exit from the examined portion 9. The scattered light L3 and the fluorescence L4 propagate through the detection optical fibers 12 and enter the optical measurement units 25. In each of the optical measurement units 25, the scattered light L3 is reflected by the dichroic mirror 26 and enters the photon-counting circuit 27. on the other hand, the fluorescence L4 passes through the dichroic mirror 26, and enters the photon-counting circuit 28. The outputs of the photon-counting circuits 27 and 28 are supplied to the signal-processing unit 30 in the signal-processing-and-control unit 17.

When the scattered incident light L2 is injected into the examined portion 9, scattered light L5 generated by further scattering of the scattered incident light L2 in the examined portion 9 and fluorescence L6 emitted from the fluorescent agent in the examined portion 9 propagate in and exit from the examined portion 9. The scattered light L5 and the fluorescence L6 propagate through the detection optical fibers 12 and enter the optical measurement units 25. In each of the optical measurement units 25, the scattered light L5 is reflected by the dichroic mirror 26 and enters the photon-counting circuit 27. On the other hand, the fluorescence L6 passes through the dichroic mirror 26 and enters the photon-counting circuit 28. The outputs of the photon-counting circuits 27 and 28 are supplied to the signal-processing unit 30 in the signal-processing-and-control unit 17.

When the unscattered incident light L1 which propagates through one of the light-injection optical fibers 10a is injected into the examined portion 9, the signal-processing unit 30 memorizes the outputs of the photon-counting circuits 27 and 28 in the ones of the optical measurement units 25 connected to the ones of the detection optical fibers 12 which are located farther from the one of the light-injection optical fibers 10a than the fiftieth detection optical fiber from the one of the detection optical fibers 12 located nearest to the one of the light-injection optical fibers 10a, and does not memorize and discards the outputs of the photon-counting circuits 27 and 28 in the other ones of the optical measurement units 25 connected to the ones of the detection optical fibers 12 which are located nearer to the one of the light-injection optical fibers 10a than the fifty-first detection optical fiber from the one of the detection optical fibers 12 located nearest to the one of the light-injection optical fibers 10a. That is, the signal-processing unit 30 memorizes the outputs of the photon-counting circuits 27 and 28 in only the ones of the optical measurement units 25 connected to the ones of the detection optical fibers 12 located vertically above a region of the examined portion 9 remote from the injection point.

When the scattered incident light L2 generated by scattering in the scatterer 18 of the unscattered incident light L1 which propagates through one of the light-injection optical fibers 10b is injected into the examined portion 9, the signal-processing unit 30 memorizes the outputs of the photon-counting circuits 27 and 28 in the ones of the optical measurement units 25 connected to the ones of the detection optical fibers 12 which are located nearer to the one of the light-injection optical fibers 10b than the fifty-first detection optical fiber from the one of the detection optical fibers 12 located nearest to the one of the light-injection optical fibers 10b, and does not memorize and discards the outputs of the photon-counting circuits 27 and 28 in the other ones of the optical measurement units 25 connected to the ones of the detection optical fibers 12 which are located farther from the one of the light-injection optical fibers 10b than the fiftieth detection optical fiber from the one of the detection optical fibers 12 located nearest to the one of the light-injection optical fibers 10b. That is, the signal-processing unit 30 memorizes the outputs of the photon-counting circuits 27 and 28 in only the ones of the optical measurement units 25 connected to the ones of the detection optical fibers 12 located vertically above a region of the examined portion 9 near to the injection point.

Since the position of the injection optical fiber through which the unscattered incident light L1 propagates is changed in succession, the near-incident-point region (i.e., the region near the incident point of the light L1 or L2) and the remote region (the region farther from the incident point of the light L1 or L2) are also changed in succession with the position of the injection optical fiber.

Figure 3:
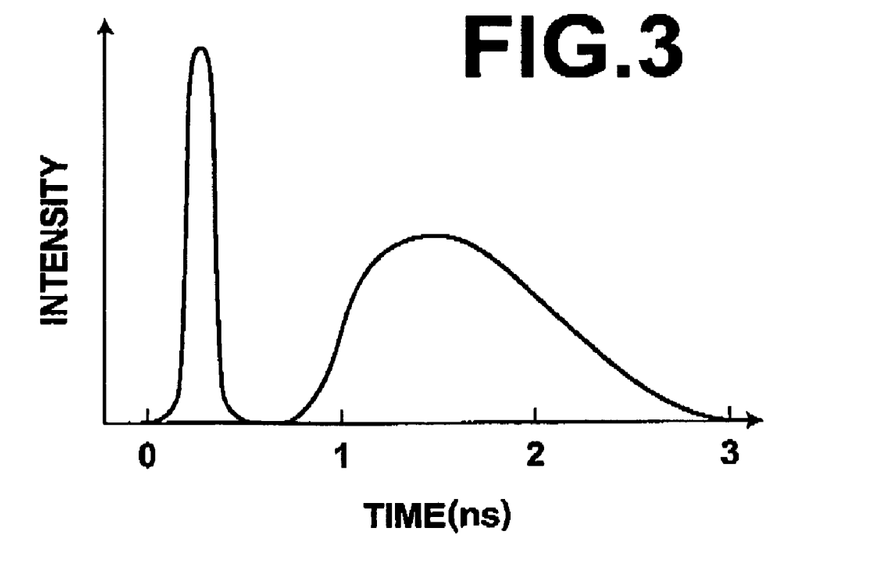
FIG. 3 is a graph indicating an example of a time profile.

Every time a million light pulses of the unscattered incident light L1 or the scattered incident light L2 are injected into one of the light-injection optical fibers 10a or 10b, the signal-processing unit 30 produces time profiles (i.e., time spreads of light caused by scattering as illustrated in FIG. 3) corresponding to each of the relevant ones of the detection optical fibers 12. That is, when a million light pulses of the unscattered incident light L1 are injected into each of the light-injection optical fibers 10a and one of the light-injection optical fibers 10b located alongside the light-injection optical fiber, a hundred time profiles of the propagated incident light L3 and L5 based on the measurement by the photon-counting circuits 27 and a hundred time profiles of the propagated fluorescence L4 and L6 based on the measurement by the photon-counting circuits 28 are produced. Thus, when a million light pulses of the unscattered incident light L1 are injected into all the light-injection optical fibers 10a and 10b, ten thousand time profiles of the propagated incident light L3 and L5 and ten thousand time profiles of the propagated fluorescence L4 and L6 are finally produced.

After the above measurement, the signal-processing unit 30 performs signal processing of the ten thousand time profiles of the incident light L3 and L5 on the basis of an optical diffusion equation, and calculates a distribution of the optical scattering coefficient and a distribution of the optical absorption coefficient in the examined portion 9. The optical scattering coefficient and the optical absorption coefficient of the scatterer 18 are memorized in the signal-processing unit 30 in advance. Next, the signal-processing unit 30 calculates a distribution of the optical scattering coefficient and a distribution of the optical absorption coefficient for light having a wavelength of 770 to 790 nm on the basis of the distribution of the optical scattering coefficient and the distribution of the optical absorption coefficient for the light having wavelength of 750 nm. Thereafter, the signal-processing unit 30 calculates the distribution of the emission sources of the fluorescence L4 (i.e., the distribution of the fluorescent agent) on the basis of the distribution of the optical scattering coefficient and the distribution of the optical absorption coefficient for light having a wavelength of 770 to 790 nm, the ten thousand time profiles of the propagated fluorescence L4 and L6, and the optical diffusion equation. The calculated distribution of the emission sources of the fluorescence L4 (i.e., the calculated distribution of the fluorescent agent) is outputted to a monitor (not shown) in the form of a tomographic image. Since the fluorescent agent has an affinity for a tumor, the tomographic image shows the shape of the tumor.

As mentioned before, in the specimen analysis system 1 according to the first embodiment, when the unscattered incident light L1 which propagates through one of the light-injection optical fibers 10a is injected into the examined portion 9, the outputs of the photon-counting circuits 27 and 28 in the ones of the optical measurement units 25 connected to the ones of the detection optical fibers 12 which are located farther from the one of the light-injection optical fibers 10a than the fiftieth detection optical fiber from the one of the detection optical fibers 12 located nearest to the one of the light-injection optical fibers 10a (i.e., in the ones of the optical measurement units 25 connected to the ones of the detection optical fibers 12 located vertically above the aforementioned region of the examined portion 9 remote from the injection point) are supplied to the signal-processing unit 30. On the other hand, when the scattered incident light L2 generated by scattering in the scatterer 18 of the unscattered incident light L1 which propagates through one of the light-injection optical fibers 10b is injected into the examined portion 9, the outputs of the photon-counting circuits 27 and 28 in ones of the optical measurement units 25 connected to ones of the detection optical fibers 12 which are located nearer to the one of the light-injection optical fibers 10b than the fifty-first detection optical fiber from the one of the detection optical fibers 12 located nearest to the one of the light-injection optical fibers 10b (i.e., in the ones of the optical measurement units 25 connected to the ones of the detection optical fibers 12 located vertically above the aforementioned region of the examined portion 9 near to the injection point) are supplied to the signal-processing unit 30. Therefore, it is possible to use the diffusion approximation even in the near-incident-point region, so that it is possible to improve the accuracy in calculation of the optical scattering coefficients and the optical absorption coefficients in the entire examined portion 9 including the near-incident-point region and the remote region without increasing the calculation time, and perform highly reliable analysis. In particular, the characteristics of the specimen in the remote region to which the diffusion approximation can be used even when unscattered light is used as the incident light is measured by using the unscattered incident light L1 as the incident light. Therefore, the intensity of the detected light becomes high, so that the accuracy in measurement of the optical scattering coefficients and the optical absorption coefficients becomes high.

The specimen analysis system 1 according to the first embodiment may be modified as follows.

(a) Although the one-dimensional fiber arrays are used for the measurement in the specimen analysis system according to the first embodiment, alternatively, it is possible to use two-dimensional fiber arrays. In this case, it is possible to obtain three-dimensional tomographic images. Further alternatively, three-dimensional tomographic images can be obtained by moving the one-dimensional fiber arrays in the direction perpendicular to the length direction of the one-dimensional fiber arrays, and repeating the measurement by use of the moved one-dimensional fiber arrays.

(b) It is possible to define a region in the range of distances equal to or smaller than 3 mm from the incident point of the incident light as the near-incident-point region, a region in the range of distances greater than 3 mm and equal to or smaller than 7 mm from the incident point as an intermediate region, and a region in the range of distances greater than 7 mm from the incident point as the remote region. In this case, the signal-processing unit 30 in the specimen analysis system 1 may be replaced with another signal-processing unit 31 which operates as follows.

For the intermediate region, the signal-processing unit 31 obtains first time profiles for each detection position based on measurement by injection of the unscattered incident light L1 into the examined portion 9 and second time profiles for each detection position based on measurement by injection of the scattered incident light L2 into the examined portion 9, adopts the first time profiles for the detection position when the difference between the first and second time profiles for the detection position does not exceed a predetermined amount, and adopts the second time profiles for the detection position when the difference between the first and second time profiles for the detection position exceeds the predetermined amount.

That is, when the difference between the first time profiles based on the measurement by injection of the unscattered incident light L1 and the second time profiles based on the measurement by injection of the scattered incident light L2 is small, the diffusion approximation can be used with the injection of the unscattered incident light L1. Since the use of the unscattered incident light L1 increases the intensity of detected light and the accuracy in measurement of the optical scattering coefficients and the optical absorption coefficients, the first time profiles based on the measurement by injection of the unscattered incident light L1 are used when the difference between the first time profiles and the second time profiles is small on the other hand, when the difference between the first time profiles and the second time profiles is great, the diffusion approximation cannot be used with the injection of the unscattered incident light L1 in some cases. Therefore, when the difference between the first and second time profiles is great, the second time profiles based on the measurement by injection of the scattered incident light L2 are used.

Figure 4:
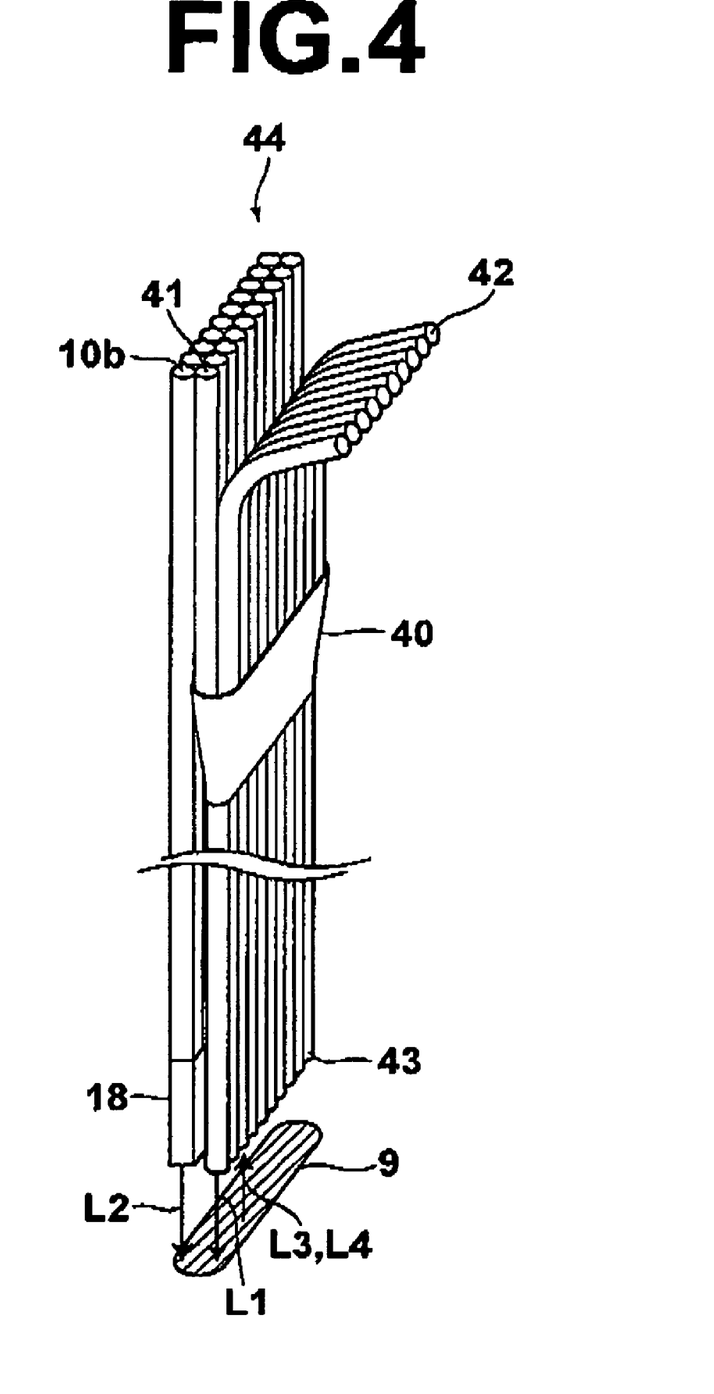
FIG. 4 is a diagram schematically illustrating a light probe.

(c) Although the specimen analysis system 1 according to the first embodiment uses the optical probe unit 14 illustrated in FIG. 1B (in which the detected-light guiding unit 13 constituted by the hundred detection optical fibers 12 is provided separately from the unscattered-incident-light injector 11a constituted by the hundred light-injection optical fibers 10a), alternatively, it is possible to use the optical probe unit 44 as illustrated in FIG. 4. In the optical probe unit 44, the unscattered-incident-light injector 11a and the detected-light guiding unit 13 are integrally joined by using an optical circulator 40. Specifically, the light-injection optical fibers 41, the detection optical fibers 42, and the injection-and-detection optical fibers 43 are coupled through the optical circulator 40, and the light-injection optical fibers 10a and the detection optical fibers 12 are not provided. The optical circulator 40 couples each of the light-injection optical fibers 41 to a corresponding one of the injection-and-detection optical fibers 43, and couples each of the injection-and-detection optical fibers 43 to a corresponding one of the detection optical fibers 42. Therefore, when the unscattered incident light L1 is applied to the examined portion 9, the connections of the light-injection optical fibers 41 and the injection-and-detection optical fibers 43 are used in succession, and the connections of the injection-and-detection optical fibers 43 and detection optical fibers 42 are used for detection of light which propagates in and exits from the examined portion 9. In addition, when the scattered incident light L2 is applied to the examined portion 9, the light-injection optical fibers 10b are used in succession, and the connections of the injection-and-detection optical fibers 43 and detection optical fibers 42 are also used for detection of light which propagates in and exits from the examined portion 9.

Figure 5:
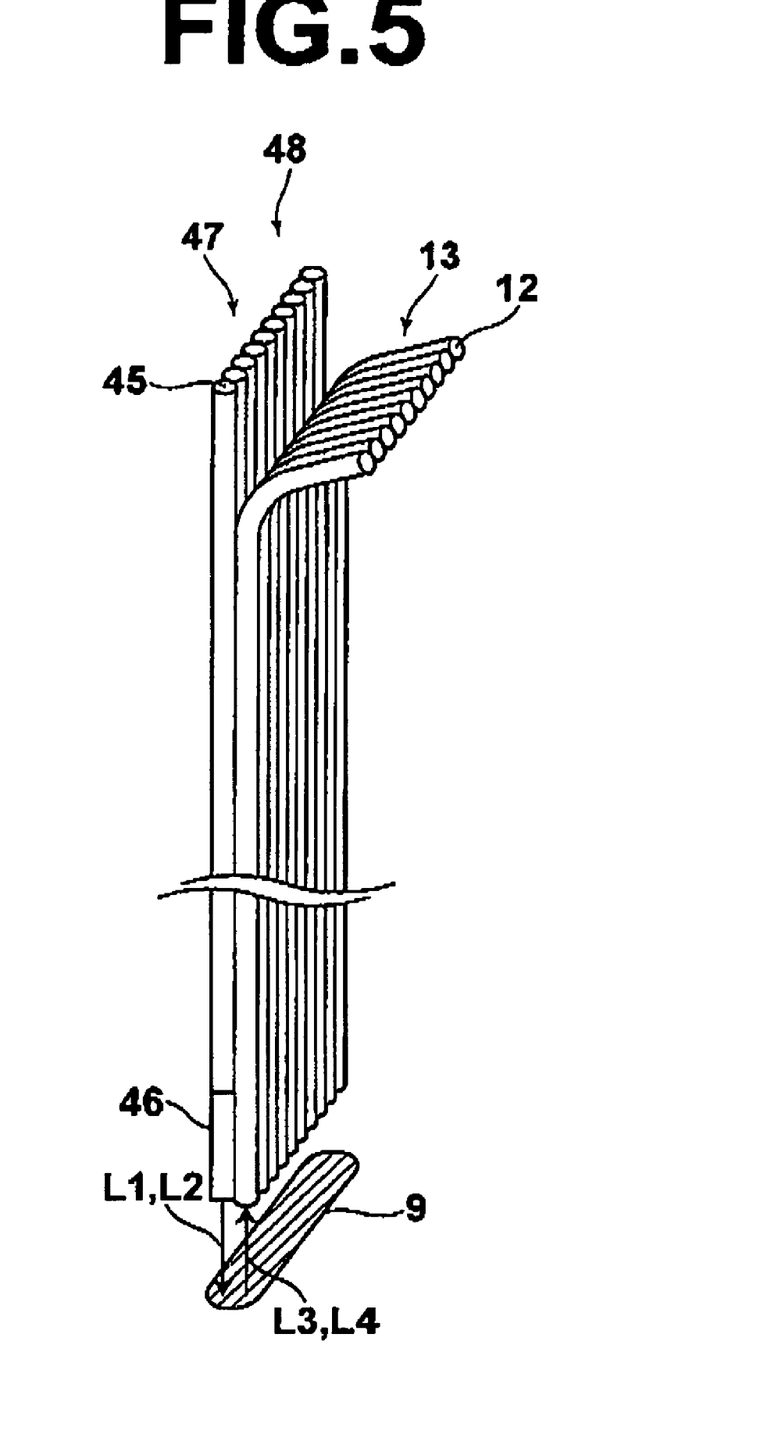
FIG. 5 is a diagram schematically illustrating a light probe.

(d) Although the specimen analysis system 1 according to the first embodiment uses the optical probe unit 14 illustrated in FIG. 1B (which is constituted by the unscattered-incident-light injector 11a and the scattered-incident-light injector 11b), alternatively, it is possible to use the optical probe unit 48 as illustrated in FIG. 5. The optical probe unit 48 comprises an incident-light injector 47, in which a variable scatterer 46 is arranged at ends of light-injection optical fibers 45 on one side, where the degree of scattering in the variable scatterer 46 can be varied. In this example, the scattering condition in the variable scatterer 46 can be varied by application of electric power, so that it is possible to alternately apply unscattered incident light and scattered incident light to the examined portion 9 through the variable scatterer 46. Specifically, it is possible to alternately realize a nonscattering condition and a high-degree scattering condition by pulsed activation of the variable scatterer 46. The use of the variable scatterer and the change of the degree of scattering between a plurality of levels for measurement enables downsizing of the optical probe unit.

Second Embodiment

A specimen analysis system according to the second embodiment of the present invention is explained below with reference to FIG. 6, which schematically shows the construction of the specimen analysis system according to the second embodiment.

The specimen analysis system 2 according to the second embodiment applies unscattered incident light L1 and scattered incident light L2 to an examined portion 9 of a subject dosed in advance with a fluorescent agent having an affinity for a tumor, and measures the distribution of the fluorescent agent in the examined portion 9, where the unscattered incident light L1 and scattered incident light L2 have wavelengths in the range which enables excitation of the fluorescent agent. The specimen analysis system 2 according to the second embodiment performs measurement by scanning a specimen with a single optical fiber for detection.

Figure 6:
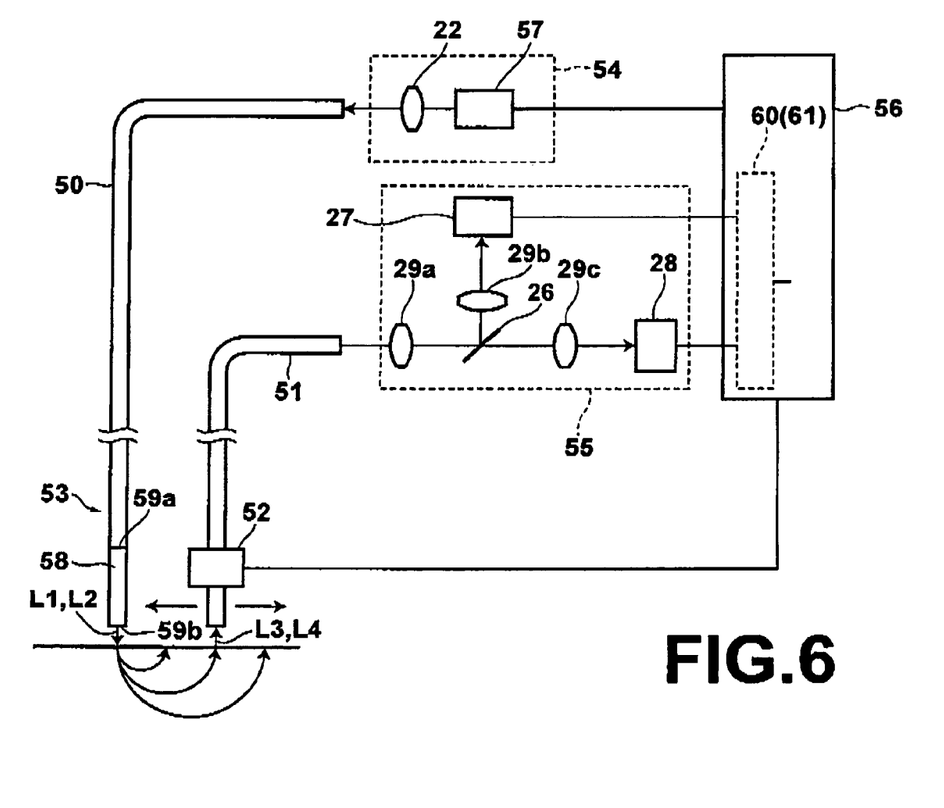
FIG. 6 is a diagram schematically illustrating a specimen analysis system according to a second embodiment of the present invention.

As illustrated in FIG. 6, the specimen analysis system 2 according to the second embodiment comprises an optical probe unit 53, a light-source unit 54, a measurement unit 55, and a signal-processing-and-control unit 56.

The optical probe unit 53 is constituted by a light-injection optical fiber 50, a variable scatterer 58, a detection optical fiber 51, and a scanning mechanism 52. The light-injection optical fiber 50 propagates unscattered incident light L1. The variable scatterer 58 is arranged at an end of the light-injection optical fiber 50, and the state of the variable scatterer 58 can be changed between a nonscattering state and a high-degree scattering state under the control of the signal-processing-and-control unit 56. The scanning mechanism 52 realizes linear scanning of the examined portion 9 with the detection optical fiber 51.

The light-injection optical fiber 50 is connected to the light-source unit 54, the detection optical fiber 51 is connected to the measurement unit 55, and the light-source unit 54 and the measurement unit 55 are connected to the signal-processing-and-control unit 56.

Each of the light-injection optical fiber 50 and the detection optical fiber 51 has a total diameter of 100 micrometers, a core diameter of 80 micrometers, and a cladding thickness of 10 micrometers. The variable scatterer 58 is formed into a bar having cross-sectional dimensions of 100×100 micrometers and a lateral length of 5 millimeters. An end of the light-injection optical fiber 50 abuts an end face 59a of the variable scatterer 58, and the opposite end face 59b of the variable scatterer 58 faces the examined portion 9.

The light-source unit 54 is constituted by a light source 57 and a lens 22. The light source 57 emits as the unscattered incident light L1 pulsed light having the wavelength of 750 nm, the pulse width of 100 ps, and the average power of 3 mW at the repetition rate of 100 MHz.

The measurement unit 55 has the same construction as each of the optical measurement units 25 in the specimen analysis system 1 according to the first embodiment.

The signal-processing-and-control unit 56 controls the overall operations of the specimen analysis system 2, and calculates the distribution of the fluorescent agent in the examined portion 9 on the basis of the outputs of the photon-counting circuits 27 and 28. Details of the operations of the signal-processing-and-control unit 56 are explained later.

The operations of the specimen analysis system 2 according to the second embodiment are explained below.

First, the optical probe unit 53 is brought into contact with the examined portion 9 of the subject, who may have a tumor. Since the optical probe unit 53 is in contact with the examined portion 9 during measurement, the end of the optical probe unit 53 on the examined-portion side is protected by a transparent protective member (not shown).

Next, the operations for measurement are started under control of the signal-processing-and-control unit 56. The light source 57 in the light-source unit 54 emits the pulsed, unscattered incident light L1 having the wavelength of 750 nm, the pulse width of 100 ps, and the average power of 3 mW at the repetition rate of 100 MHz. The signal-processing-and-control unit 56 controls the scanning mechanism 52 so that the detection optical fiber 51 is initially located alongside the light-injection optical fiber 50, and is linearly moved away from the position adjacent to the light-injection optical fiber 50 by 100 micrometers every time a million successive light pulses are injected through the light-injection optical fiber 50. The movement of the detection optical fiber 51 is repeated one hundred times.

In addition, the signal-processing-and-control unit 56 comprises a signal-processing unit 60, and controls the variable scatterer 58 so that the variable scatterer 58 is in the scattering state while the initial fifty million light pulses (i.e., the first half of the hundred million light pulses) are outputted from the light-source unit 54, and in the nonscattering state while the subsequent fifty million light pulses (i.e., the second half of the hundred million light pulses) are outputted from the light-source unit 54. Therefore, the scattered incident light L2 (which is produced through the variable scatterer 58. in the scattering state) is injected into the examined portion 9 while the detection optical fiber 51 is located within 5 millimeters of the light-injection optical fiber 50 (i.e., while the first half of the hundred million light pulses are outputted from the light-source unit 54), and the unscattered incident light L1 (which passes through the variable scatterer 58 in the nonscattering state) is injected into the examined portion 9 while the detection optical fiber 51 is more than 5 millimeters apart from the light-injection optical fiber 50 (i.e., while the second half of the hundred million light pulses are outputted from the light-source unit 54).

The optical measurement units 55 performs a photon-counting operation every time a light pulse is outputted from the light-source unit 54. In response to each light pulse outputted from the light-source unit 54, the scattered light L5 or L3 and the fluorescence L6 or L4 propagate in and exit from the examined portion 9, where the scattered light L5 is produced by scattering of the scattered incident light L2 in the examined portion 9, the fluorescence L6 is emitted from the fluorescent agent in the examined portion 9 which is excited by the scattered incident light L2, the scattered light L3 is produced by scattering of the unscattered incident light L1 in the examined portion 9, and the fluorescence L4 is emitted from the fluorescent agent in the examined portion 9 which is excited by the unscattered incident light L1.

The scattered light L5 or L3 and the fluorescence L6 or L4 pass through the detection optical fiber 51, and enter the measurement unit 55. In the measurement unit 55, the scattered light L5 or L3 is reflected by the dichroic mirror 26, and enters the photon-counting circuit 27. On the other hand, the fluorescence L6 or L4 passes through the dichroic mirror 26, and enters the photon-counting circuit 28. The outputs. of the photon-counting circuits 27 and 28 are supplied to the signal-processing unit 60 in the signal-processing-and-control unit 56.

The signal-processing unit 60 produces time profiles (i.e., time spreads of light caused by scattering) on the basis of the outputs of the photon-counting circuits 27 and 28 as illustrated in FIG. 3. Since the hundred million light pulses are injected into the examined portion 9 in total while the detection optical fiber 51 moves through the hundred positions, a hundred time profiles of the scattered light L3 and L5 and a hundred time profiles of the fluorescence L4 and L6 are finally produced.

After the above measurement, the signal-processing unit 60 performs signal processing of the hundred time profiles of the scattered light L3 and L5 on the basis of the optical diffusion equation, and calculates a distribution of the optical scattering coefficient and a distribution of the optical absorption coefficient in the examined portion 9 for the light having wavelength of 750 nm. The optical scattering coefficients and the optical absorption coefficients of the variable scatterer 58 are memorized in the signal-processing unit 60 in advance. Next, the signal-processing unit 60 calculates a distribution of the optical scattering coefficient and a distribution of the optical absorption coefficient for light having a wavelength of 770 to 790 nm on the basis of the distribution of the optical scattering coefficient and the distribution of the optical absorption coefficient for the light having wavelength of 750 nm. Thereafter, the signal-processing unit 60 calculates the distribution of the emission sources of the fluorescence L4 (i.e., the distribution of the fluorescent agent) on the basis of the distribution of the optical scattering coefficient and the distribution of the optical absorption coefficient for light having a wavelength of 770 to 790 nm, the hundred time profiles of the propagated fluorescence L4 and L6, and the optical diffusion equation. The calculated distribution of the emission sources of the fluorescence L4 is outputted to a monitor (not shown) in the form of a tomographic image. Since the fluorescent agent has an affinity for a tumor, the tomographic image shows the shape of the tumor. Since the number of the produced time profiles is small according to the second embodiment, the processing time and the time necessary for acquiring the tomographic image are reduced, although the obtained tomographic image is simplified.

As mentioned before, in the specimen analysis system 2 according to the second embodiment, the diffusion approximation can be used even in the near-incident-point region, so that it is possible to improve the accuracy in calculation of the optical scattering coefficients and the optical absorption coefficients in the entire examined portion 9 including the near-incident-point region and the remote region without increasing the calculation time, and perform highly reliable analysis.

The specimen analysis system 2 according to the second embodiment may be modified as follows.

(a) Although the detection optical fiber 51 is one-dimensionally moved in the above explanations of the specimen analysis system 2 according to the second embodiment, it is possible to two-dimensionally move the detection optical fiber 51. In this case, it is possible to obtain three-dimensional tomographic images.

(b) The signal-processing unit 60 in the specimen analysis system 2 according to the second embodiment may be replaced with a signal-processing unit 61, which operates as follows. That is, the signal-processing unit 61 controls the specimen analysis system 2 so as to perform first measurement by injection of the unscattered incident light L1 into the examined portion 9 and second measurement by injection of the scattered incident light L2 into the examined portion 9, and thereafter obtains first time profiles based on the first measurement and second time profiles based on the second measurement. In addition, the signal-processing unit 61 adopts the first time profiles when the difference between the first and second time profiles for the detection position does not exceed a predetermined amount, and adopts the second time profiles when the difference between the first and second time profiles for the detection position exceeds the predetermined amount.

That is, when the difference between the first time profiles based on the first measurement by injection of the unscattered incident light L1 and the second time profiles based on the second measurement by injection of the scattered incident light L2 is small, the diffusion approximation can be used with the injection of the unscattered incident light L1. Therefore, in this case, the first time profiles based on the first measurement by injection of the unscattered incident light L1 are used since the use of the unscattered incident light L1 increases the intensity of detected light and the accuracy in measurement of the optical scattering coefficients and the optical absorption coefficients. On the other hand, when the difference between the first time profiles based on measurement by injection of the unscattered incident light L1 and the second time profiles based on measurement by injection of the scattered incident light L2 is great, the diffusion approximation cannot be used with the injection of the unscattered incident light L1 in some cases. Therefore, when the difference between the first and second time profiles is great, the second time profiles based on the second measurement by injection of the scattered incident light L2 are used.

(c) It is possible to use as the variable scatterer 58 a scatterer in which the degree of scattering can be continuously varied, and continuously vary the degree of scattering in the variable scatterer 58 according to the magnitude of the difference between the first time profiles based on the first measurement by injection of the unscattered incident light L1 and the second time profiles based on the second measurement by injection of the scattered incident light L2. Specifically, the degree of scattering in the variable scatterer 58 is minimized when the difference between the first time profiles and the second time profiles is very small, and increased with the magnitude of the difference. In this case, it is possible to perform measurement by using light which is scattered to such a degree as to enable use of the diffusion approximation, and improve the accuracy in calculation of the characteristic in the entire volume of the specimen including the vicinity of the incident point of the light and other regions far from the incident point while securing a necessary intensity of the light and avoiding increase in the time necessary for the calculation.

Additional Matters

Although the present invention is applied to the measurement systems using the time-resolved spectroscopy according to the first and second embodiments, the present invention can also be applied to measurement systems using the frequency-domain spectroscopy, for example, by using high-frequency modulated light as the incident light, and measuring intensity variations and phase delays of detected scattered light and fluorescence.

What is claimed is:

1. A specimen analysis system comprising:
   a light injection unit which selectively injects unscattered light and scattered light into a specimen at an incident position on the specimen, where the scattered light is generated by scattering by a scattering medium;
   an information acquisition unit which acquires first information carried by first light exiting from a plurality of positions in a first region of said specimen in response to injection of said scattered light into the specimen, and second information carried by second light exiting from a plurality of positions in a second region of the specimen in response to injection of said unscattered light into the specimen, where the first region is located within a predetermined distance from said incident position, and the second region is located farther from the incident position than the first region; and
   an information processing unit which calculates a characteristic of said specimen by diffusion approximation, where calculation of the characteristic in said first region is based on said first information, and calculation of the characteristic in said second region is based on said second information.

2. A specimen analysis system according to claim 1, wherein said light injection unit alternately applies said unscattered light and said scattered light to said specimen.

3. A specimen analysis system according to claim 2, wherein said information acquisition unit further acquires third information carried by third light exiting from a plurality of positions in a third region of said specimen in response to injection of said unscattered light into the specimen, and fourth information carried by fourth light exiting from a plurality of positions in the third region of the specimen in response to injection of said scattered light into the specimen, where the third region is located farther from the incident position than the first region and nearer to the incident position than the second region, and said information processing unit compares the third information and the fourth information, and calculates the characteristic in said third region on the basis of said third information when a difference between the third information and the fourth information is equal to or smaller than a predetermined amount, and on the basis of said fourth information when the difference between the third information and the fourth information is greater than the predetermined amount.

4. A specimen analysis system according to claim 3, wherein said first light, said second light, said third light, and said fourth light include fluorescence emitted from said specimen.

5. A specimen analysis system according to claim 2, wherein said first light and said second light include fluorescence emitted from said specimen.

6. A specimen analysis system according to claim 1, wherein said information acquisition unit further acquires third information carried by third light exiting from a plurality of positions in a third region of said specimen in response to injection of said unscattered light into the specimen, and fourth information carried by fourth light exiting from a plurality of positions in the third region of the specimen in response to injection of said scattered light into the specimen, where the third region is located farther from the incident position than the first region and nearer to the incident position than the second region, and said information processing unit compares the third information and the fourth information, and calculates the characteristic in said third region on the basis of said third information when a difference between the third information and the fourth information is equal to or smaller than a predetermined amount, and on the basis of said fourth information when the difference between the third information and the fourth information is greater than the predetermined amount.

7. A specimen analysis system according to claim 6, wherein said first light, said second light, said third light, and said fourth light include fluorescence emitted from said specimen.

8. A specimen analysis system according to claim 1, wherein said first light and said second light include fluorescence emitted from said specimen.

9. A specimen analysis system comprising:
- a light injection unit which contains a scattering medium scattering unscattered light to a degree of scattering which can be controlled stepwise or continuously, produces first light and second light by scattering the unscattered light with the scattering medium to first and second degrees of scattering, respectively, and selectively injects the first light and the second light into a specimen at an incident position on the specimen, where the first degree of scattering is higher than the second degree of scattering;
- a scattering control unit which controls the degree Of scattering in the scattering medium;
- an information acquisition unit which acquires first information carried by third light exiting from a plurality of positions in a first region of said specimen in response to injection of said first light into the specimen, and second information carried by fourth light exiting from a plurality of positions in a second region of the specimen in response to injection of said second light into the specimen, where the first region is located within a predetermined distance from said incident position, and the second region is located farther from the incident position than the first region; and
- an information processing unit which calculates a characteristic of said specimen by diffusion approximation, where calculation of the characteristic in said first region is based on said first information, and calculation of the characteristic in said second region is based on said second information.

10. A specimen analysis system according to claim 9, wherein said information processing unit performs a comparison between said first information and said second information, and controls the degree of scattering in the scattering medium according to a result of the comparison.

11. A specimen analysis system according to claim 10, wherein said third light and said fourth light include fluorescence emitted from said specimen.

12. A specimen analysis system according to claim 9, wherein said third light and said fourth light include fluorescence emitted from said specimen.

* * * * *